United States Patent
Higuchi

(10) Patent No.: US 10,657,399 B2
(45) Date of Patent: May 19, 2020

(54) BIOMETRIC IMAGING DEVICE, BIOMETRIC IMAGING METHOD AND PROGRAM

(71) Applicant: NEC Corporation, Minato-ku, Tokyo (JP)

(72) Inventor: Teruyuki Higuchi, Tokyo (JP)

(73) Assignee: NEC CORPORATION, Tokyo (JP)

(*) Notice: Subject to any disclaimer, the term of this patent is extended or adjusted under 35 U.S.C. 154(b) by 0 days.

(21) Appl. No.: 15/519,362

(22) PCT Filed: Oct. 23, 2015

(86) PCT No.: PCT/JP2015/079937
§ 371 (c)(1),
(2) Date: Apr. 14, 2017

(87) PCT Pub. No.: WO2016/063971
PCT Pub. Date: Apr. 28, 2016

(65) Prior Publication Data
US 2017/0236018 A1  Aug. 17, 2017

(30) Foreign Application Priority Data

Oct. 24, 2014  (JP) .................................. 2014-216793

(51) Int. Cl.
G06K 9/00 (2006.01)
A61B 5/117 (2016.01)
A61B 5/1172 (2016.01)

(52) U.S. Cl.
CPC .......... *G06K 9/00885* (2013.01); *A61B 5/117* (2013.01); *A61B 5/1172* (2013.01); *G06K 9/00013* (2013.01); *G06K 9/00912* (2013.01); *G06K 2009/00932* (2013.01)

(58) Field of Classification Search
None
See application file for complete search history.

(56) References Cited

U.S. PATENT DOCUMENTS

| | | | |
|---|---|---|---|
| 8,639,214 B1* | 1/2014 | Fujisaki | G06Q 20/32 379/88.03 |
| 2006/0190836 A1* | 8/2006 | Ling Su | G06F 1/1616 715/773 |
| 2009/0185726 A1 | 7/2009 | Higuchi | |

(Continued)

FOREIGN PATENT DOCUMENTS

| JP | H07-021373 A | 1/1995 |
|---|---|---|
| JP | H09-274656 A | 10/1997 |

(Continued)

OTHER PUBLICATIONS

International Search Report for PCT Application No. PCT/JP2015/079937, dated Dec. 1, 2015.

(Continued)

*Primary Examiner* — Jiangeng Sun

(57) ABSTRACT

A biometric imaging device is provided with: placement unit that supports a biological object, imaging unit that takes images of the biological object, and determining unit that determines whether or not the biological object is placed on the placement unit, based on whether or not a feature of the biological object has changed at a place where the placement unit and the biological object are in contact, in the image(s).

17 Claims, 14 Drawing Sheets

(56) References Cited

U.S. PATENT DOCUMENTS

| | | | |
|---|---|---|---|
| 2009/0252387 A1 | 10/2009 | Higuchi | |
| 2010/0275267 A1* | 10/2010 | Walker | G07F 9/023 726/26 |
| 2011/0129128 A1* | 6/2011 | Makimoto | G06K 9/00013 382/124 |
| 2012/0114195 A1 | 5/2012 | Matsuda et al. | |

FOREIGN PATENT DOCUMENTS

| | | |
|---|---|---|
| JP | 2003-085538 A | 3/2003 |
| JP | 2003-132341 A | 5/2003 |
| JP | 2005-025414 A | 1/2005 |
| JP | 2005-253989 A | 9/2005 |
| JP | 2008-022973 A | 2/2008 |
| JP | 2009-175810 A | 8/2009 |
| JP | 2009-252052 A | 10/2009 |
| JP | 2012-098974 A | 5/2012 |
| JP | 2013-003735 A | 1/2013 |
| JP | 2014-102845 A | 6/2014 |
| WO | 2012/063761 A1 | 5/2012 |

OTHER PUBLICATIONS

Japanese Office Action for JP Application No. 2018-136975 dated Jul. 23, 2019 with English Translation.

\* cited by examiner

BIOMETRIC IMAGING DEVICE, BIOMETRIC IMAGING METHOD AND PROGRAM

REFERENCE RELATED APPLICATION

The present invention is based upon and claims the benefit of the priority of Japanese patent application No. 2014-21679, filed on Oct. 24, 2014, the disclosures of which are incorporated herein in their entirety by reference thereto.

The present invention relates to a biometric imaging device, a biometric imaging method and a program, and in particular relates to a biometric imaging device, a biometric imaging method and a program, where an image is taken of a feature of a biological object, to be used for personal authentication.

BACKGROUND

In recent years in order to prevent leakage of business information, there are increasing demands with regard to login commands to personal computers and to controlling entering or exiling rooms. However, since impersonation (or spoofing) is relatively easy with regard to methods of inputting passwords and inserting cards, there is increasing usage of control methods using features of biological objects with which impersonation is difficult.

For example, as an authentication device to authenticate individuals by placing a finger on the device, systems are known in which a surface skin pattern such as a fingerprint or a vein pattern are collated.

Patent Literature 1 discloses a non-contact personal identification device that uses a fingerprint as a biometric feature.

Patent Literature 2 discloses a non-contact personal identification device that uses a finger blood vessel as a biometric feature.

Patent Literature 3 and 4 disclose an authentication imaging device that obtains a fingerprint image and blood vessel image to realize high authentication accuracy.

Patent Literature 5 discloses technology in which, in a biometric authentication device that simultaneously takes fingerprint and vein images, a sensor for detecting placement of the tip region and the base of a finger is provided, and when the tip region and the base of the finger are not in a normal placement, notification of an abnormality in the finger placement is given to a user by flashing a lamp.

Patent Literature 6 discloses technology in which, in order to prevent reduced reproducibility when authentication is performed, due to blood flow being halted when a finger is presented on a guide part and the finger is in pressurized contact with the guide part so that there is a partial lack of a blood vessel pattern, the region used in authentication does not make contact with the device while the finger position is held.

Patent Literature 7 discloses a biometric authentication device in which a detection sensor is provided that makes contact with a prescribed part of a person, and outputs a signal in accordance with the level of pressure by the prescribed part (level of pressing force applied, extent of color change of finger due to pressure, or the like), and a determination is made as to whether or not the state of the prescribed part is one in which hand print information and vein information should be obtained, in accordance with a signal from the detection sensor.

[PTL 1]
Japanese Patent Kokai Publication No. JP2003-085538A
[PTL 2]
Japanese Patent Kokai Publication No. JP-H07-021373A
[PTL 3]
Japanese Patent Kokai Publication No. JP2009-175810A
[PTL 4]
Japanese Patent Kokai Publication No. JP 2009-252052A
[PTL 5]
International Publication No. WO2012/063761
[PTL 6]
Japanese Patent Kokai Publication No. JP2012-098974A
[PTL 7]
Japanese Patent Kokai Publication No. JP2014-102845A

SUMMARY

The entire disclosed content of the abovementioned Patent Literatures are incorporated herein by reference thereto. The following analysis is given according to the present inventor.

According to biometric feature input devices described in Patent Literature 1 to 4, there may be situations where the time of pulling away an operator's finger is too early, or the finger base region or fingertip region alone is raised. In such a case, there is a problem in that an image is inputted when the finger is partially or completely taken away from an imaging device in operation, focusing does not take place properly and the image is blurred, or the image is small and authentication accuracy decreases.

The devices described in Patent Literature 3 to 5 are used in collating both the fingerprint and blood vessel (termed as "vein" herein) of a finger. Therefore, these devices have greater ability to detect a fake finger (replica) than an input device that uses a single biometric feature. However, there is a problem in that even with these devices, it is not possible to detect a fake finger made by copying both the fingerprint and veins of a finger.

Furthermore, in the device described in Patent Literature 5, a sensor is provided for detecting the placement of the tip region (fingertip region) and the base region (finger base region) of a finger, and there is a problem in that the cost of the device increases as the device configuration becomes more complex.

Patent Literature 6 merely discloses technology to prevent the lack of a vein pattern according to contact between a guide part and a finger, and does not disclose technology that actively uses the lack of a vein pattern.

According to the technology described in Patent Literature 7, for a place where a biometric object (for example, a finger) and a placement unit to support the biometric object (a hand print information acquisition unit in Patent Literature 7), it is not possible to obtain a feature outside of a hand print (for example, veins or a profile), and there is a risk that authentication accuracy will decrease.

Therefore, when an image of a biometric feature is taken in order to be used for personal authentication, a problem is that of improving the accuracy of authentication based on the biometric feature whose image is taken, as the same time as enabling the taking of an image of the biometric feature at appropriate timing. It is an object of the present invention to provide a biometric imaging device, a biometric imaging method and a program, which contribute towards solving this problem.

According to a first aspect of the present invention, a biometric imaging device is provided with: a placement unit that supports a biological object; an imaging unit that takes images of the biological object; and a determining unit that determines whether or not the biological object is placed on the placement unit, based on whether or not a feature of the biological object has changed at a place where the placement unit and the biological object are in contact, in the image(s).

According to a second aspect of the present invention, a biometric imaging method includes: taking images of a biological object, by a biometric imaging device; and determining whether or not the biological object is placed on a placement unit, based on whether or not a feature of the biological object has changed at a place where the biological object and the placement unit that supports the biological object are in contact, in the image(s).

According to a third aspect of the present invention, a program executes on a computer: a process of taking images of a biological object; and a process of determining whether or not the biological object is placed on a placement unit, based on whether or not a feature of the biological object has changed at a place where the biological object and the placement unit that supports the biological object are in contact, in the image(s). It is to be noted that the program may be provided as a program product recorded on a non-transitory computer-readable storage medium.

According to the biometric imaging device, the biometric imaging method and the program of the present invention, when images of a biometric feature are taken in order to be used for personal authentication, the taking of images of the biometric feature is enabled at appropriate timing and, at the same time, the accuracy of authentication based on the biometric feature whose images have been taken, is improved.

PREFERRED MODES

Figure 1:
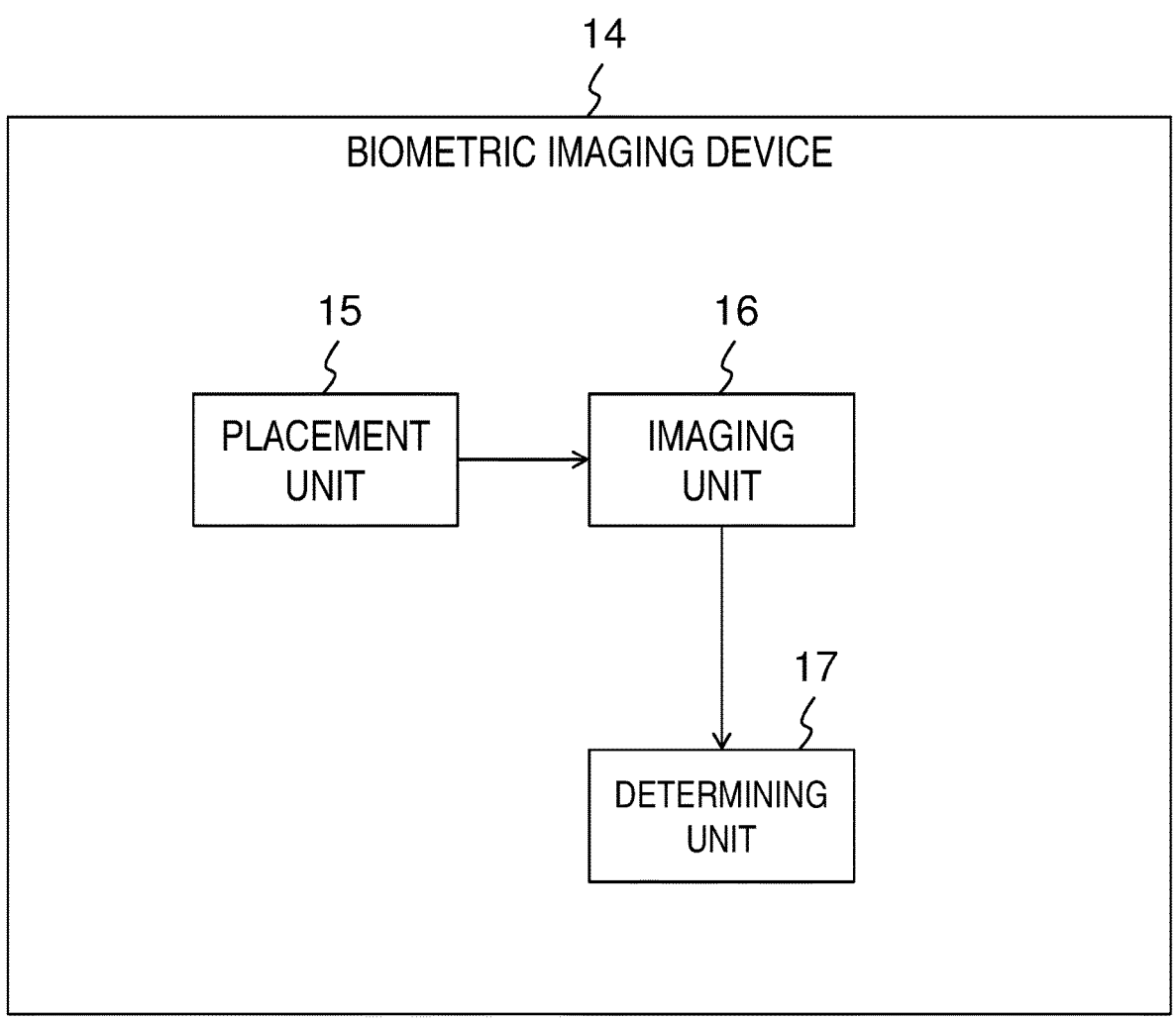
FIG. 1 is a block diagram showing an example of a configuration of a biometric imaging device according to an exemplary embodiment.

First, a description is given concerning an outline of an exemplary embodiment. It is to be noted that reference symbols in the drawings attached to this outline are examples solely for the purpose of aiding understanding, and are not intended to limit the present invention to modes illustrated in the drawings.

FIG. 1 is a block diagram showing an example of a configuration of a biometric imaging device 14 according to the exemplary embodiment. Referring to FIG. 1, the biometric imaging device 14 is provided with a placement unit 15, an imaging unit 16 and a determining unit 17.

The placement unit 15 supports a biometric object (for example, a finger or hand palm of an operator). The imaging unit 16 takes an image of the biometric object (for example, a finger or hand palm). The determining unit 17 determines whether or not the biometric object is placed on the placement unit 15, based on whether or not a feature of the biometric object has changed at a place where the placement unit 15 and the biometric object are in contact.

According to the biometric imaging device 14, when an image of a biometric feature is taken to be used for personal authentication, imaging of the biometric feature is enabled at appropriate timing, and at the same time the accuracy of authentication based on the biometric feature whose image has been taken is improved. This is because it is possible to take an image(s) at appropriate timing(s) with regard to the biometric object being placed, by determining whether or not a feature of the biometric object has changed at a place where the placement unit 15 and the biometric object come into contact. This is also because, by taking image(s) of a biometric feature (for example, veins and/or profile) at a place where the placement unit 15 and the biometric object are in contact, it is possible to improve authentication accuracy in comparison with a case of obtaining only an image of a hand print at a place where the placement unit 15 and the biometric object are in contact as in Patent Literature 7.

Also, the determining unit 17 may determine whether or not a finger or hand palm is placed on the placement unit 15, based on whether or not vein(s) of the finger or hand palm and/or the profile of the finger or hand palm have changed in the image(s).

According to the biometric imaging device 14 in question, by determining whether or not a finger or hand palm is placed on the placement unit 15 based on whether or not a feature of the finger or hand palm (for example, vein of the finger or a hand palm; a profile of the finger or hand palm) has changed in the image(s), it is possible to prevent a situation where timing at which an operator removes his/her finger is too early, or the finger base region or fingertip region only is floating (i.e., not in contact). In this way, it is possible to obtain appropriate images, and it is possible to improve the accuracy of authentication. According to this configuration, it is possible to detect even a finger replica made by copying both a fingerprint and vein(s) of a finger. This is because with the replica, there is no change in (or between) the image(s) of the finger vein(s) before and after being placed on the placement unit. Furthermore, according to this configuration, there is no necessity to provide a sensor as in Patent Literature 5, and it is possible to simplify the device configuration. Therefore, according to the biometric imaging device 14, in an authentication device that performs personal authentication based on an image(s) taken of a biometric feature, it is possible to improve authentication accuracy based on a simple device configuration.

Figure 2:
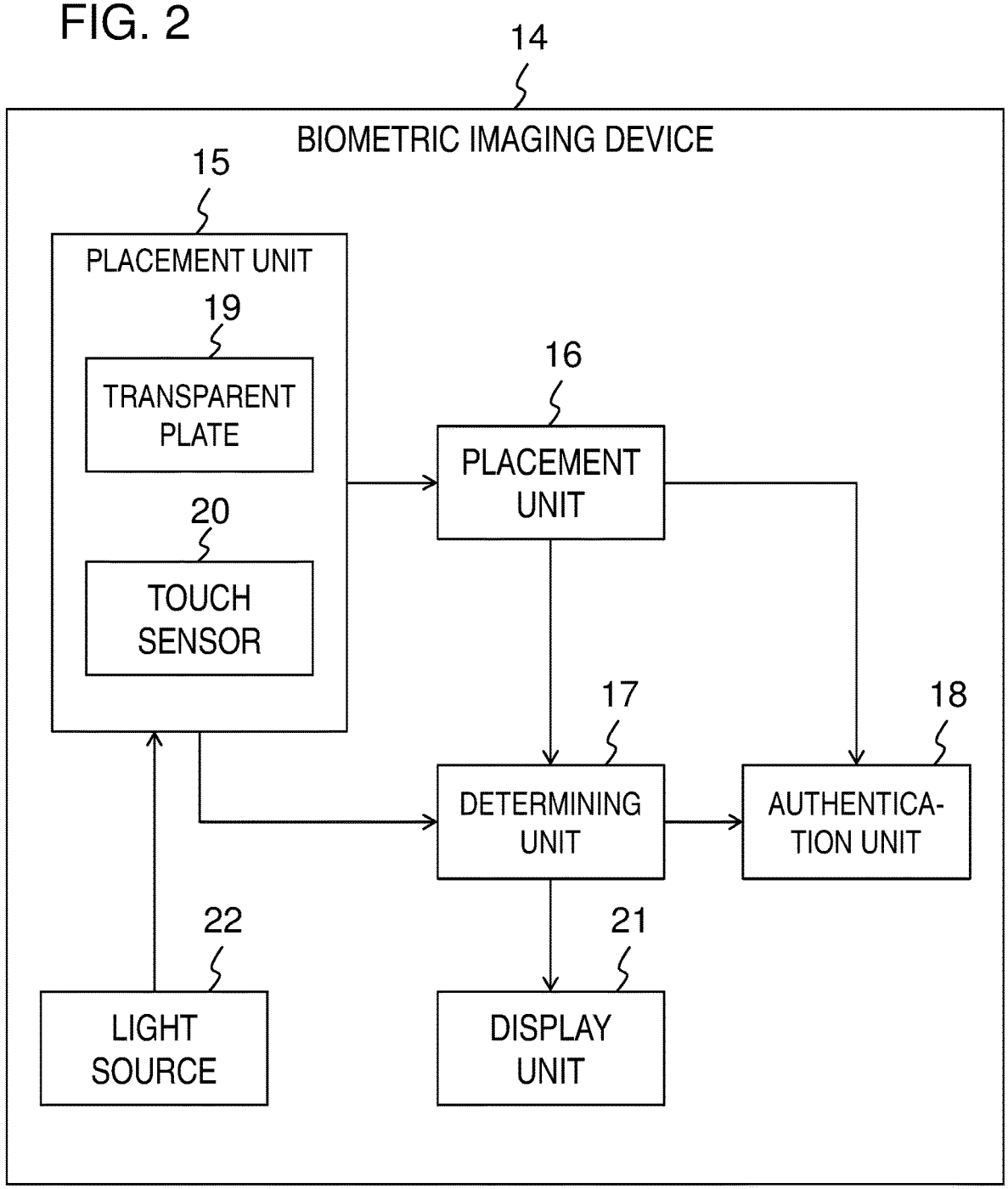
FIG. 2 is a block diagram showing an example of another configuration of the biometric imaging device according to an exemplary embodiment.

FIG. 2 is a block diagram showing an example of another configuration of the biometric imaging device according to an exemplary embodiment. Referring to FIG. 2, the biometric imaging device 14 is further provided with an authentication unit 18, a display unit 21 and a light source 22. A placement unit 15 is provided with a transparent plate 19 and a touch sensor 20. In a case where it is determined that a finger or a hand palm is placed on the placement unit 15, the authentication unit 18 performs personal authentication based at least any one of: vein of a finger or hand palm, a fingerprint, and a palm print, included in an image.

Figure 4:
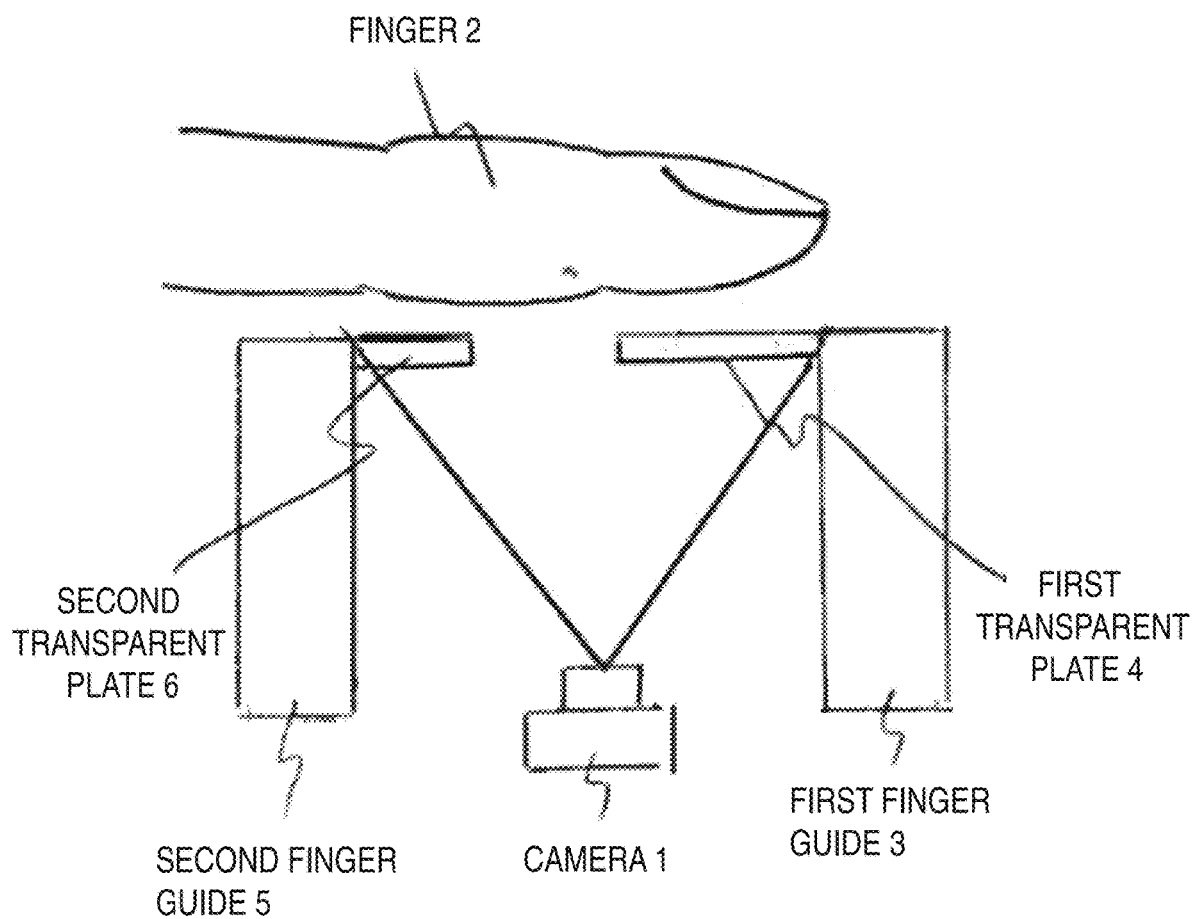
FIG. 4 is a front view of an example showing a configuration and layout of a camera and a placement unit in the biometric imaging device according to the first and second exemplary embodiments.

The transparent plate 19 (for example, a first transparent plate 4, a second transparent plate 6 in FIG. 4) supports at least a part of a finger or a hand palm. At this time, an imaging unit 16 (for example, a camera 1 in FIG. 4) may take an image of a place where the finger or hand palm is in contact with a transparent plate and of a place where they are not in contact. At the place where, in the image(s), the transparent plate and the finger or hand palm are in contact, the determining unit 17 may make also a determination as to whether or not the finger or hand palm is placed on the placement unit 15, based on whether or not the width of the profile of the finger or hand palm, and/or the vein of the finger or hand palm has changed.

By providing a transparent plate in the placement unit 15, even in a case where the finger or hand palm is not pressed strongly against the placement unit 15, it is possible to relatively easily detect a change in the width of the profile of the finger or hand palm, or the vein of the finger or hand palm.

Figure 9:
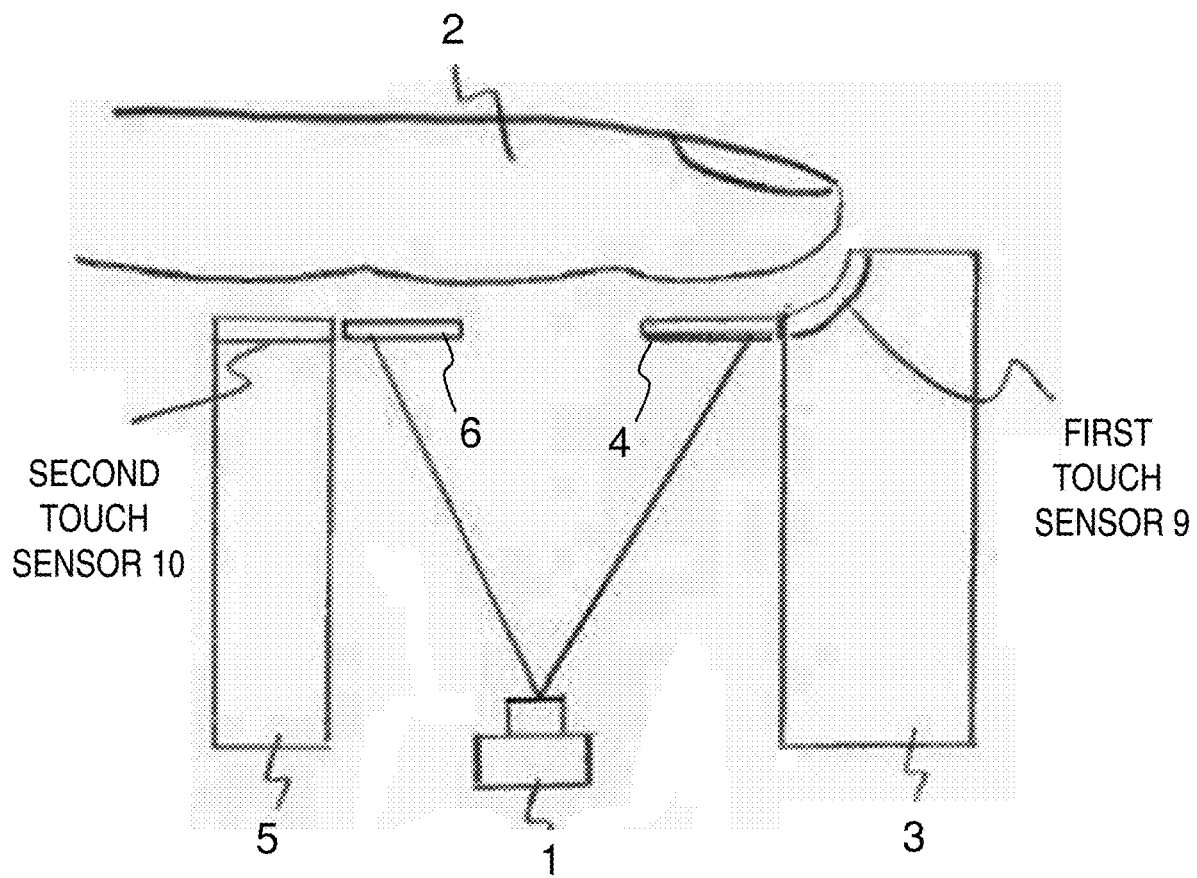
FIG. 9 is a front view of an example showing a configuration and layout of a camera and a placement unit in the biometric imaging device according to the third exemplary embodiment.

A touch sensor 20 (for example, a first touch sensor 9 or a second touch sensor 10, in FIG. 9) detects contact with the finger or hand palm. At this time, the determining unit 17 may also determine whether or not the finger or hand palm is placed on the placement unit 15, based on whether or not the width and/or vein has changed, and also a detection result of the touch sensor 20.

By providing the touch sensor 20, it is possible to more accurately determine that a finger or hand palm is placed on the placement unit 15 in comparison with a case of determining whether or not a finger or a hand palm is placed on the placement unit 15, based on only whether or not a feature of the finger or hand palm (for example, vein, profile, or the like) has changed in an image.

In addition, the display unit 21 (for example, a first indicator 7 or second indicators 8, in FIG. 5 or FIG. 10) preferably makes a display prompting that a finger or hand palm be placed on the placement unit 15, in a case of determining that a finger or hand palm is not placed on the placement unit 15.

By providing such display unit 21, it is possible to prevent the timing at which an operator removes a finger being too early, or to prevent a finger base region or fingertip region alone from floating (i.e., separating), and it is possible to avoid an image being blurred (out of focus) or an image being small, and authentication accuracy decreasing.

Furthermore, the light source 22 preferably radiates light of wavelength 650 nm to 900 nm on a finger or hand palm via the transparent plate 19. By radiating light of this wavelength on the finger or hand palm, it is possible to obtain a clear image of a vein.

First Exemplary Embodiment

Figure 3:
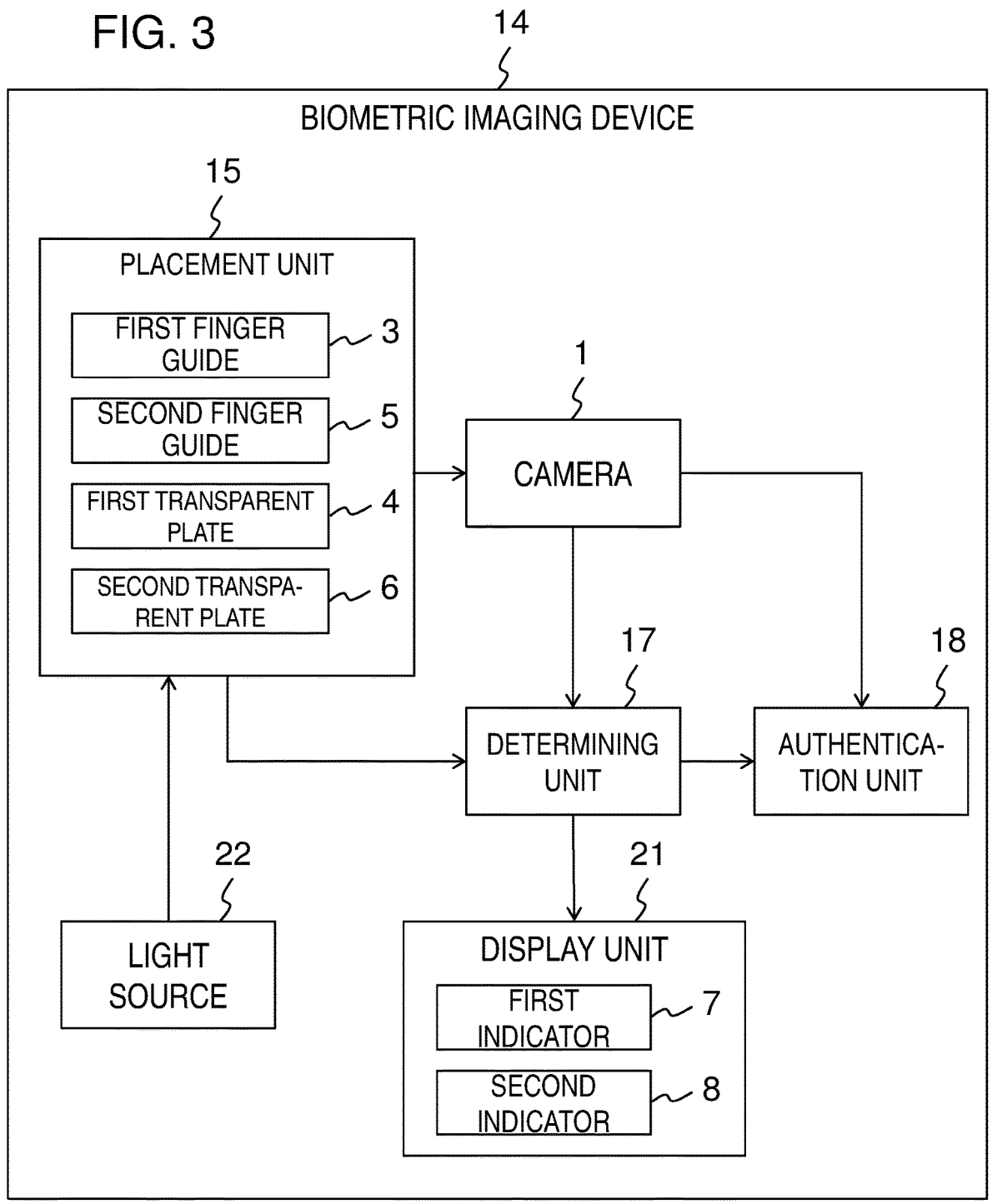
FIG. 3 is a block diagram showing an example of a configuration of the biometric imaging device according to first and second exemplary embodiments.

Next, a description is given concerning a biometric imaging device according to a first exemplary embodiment, making reference to the drawings. FIG. 3 is a block diagram showing an example of a configuration of a biometric imaging device 14 according to the present exemplary embodiment. Referring to FIG. 3, the biometric imaging device 14 is provided with a placement unit 15, a camera 1, a determining unit 17, an authentication unit 18, a display unit 21 and a light source 22. The placement unit 15 has a first finger guide 3, a second finger guide 5, a first transparent plate 4, and a second transparent plate 6. Furthermore, the display unit 2 has a first indicator 7 and second indicators 8.

FIG. 4 is a front view of an example showing a configuration and layout of the camera 1 and the placement unit 15 of the biometric imaging device 14. Referring to FIG. 4, the camera 1 takes an image of a finger 2, and reads vein or fingerprint of the finger 2 as an image. The first finger guide 3 is a guide that supports the fingertip region of the finger 2, and has the first transparent plate 4 with which the fingertip region of the finger 2 makes contact. Meanwhile, the second finger guide 5 is a guide that supports the finger base region of the finger 2, and has the second transparent plate 6 with which the finger base region makes contact.

Figure 5:
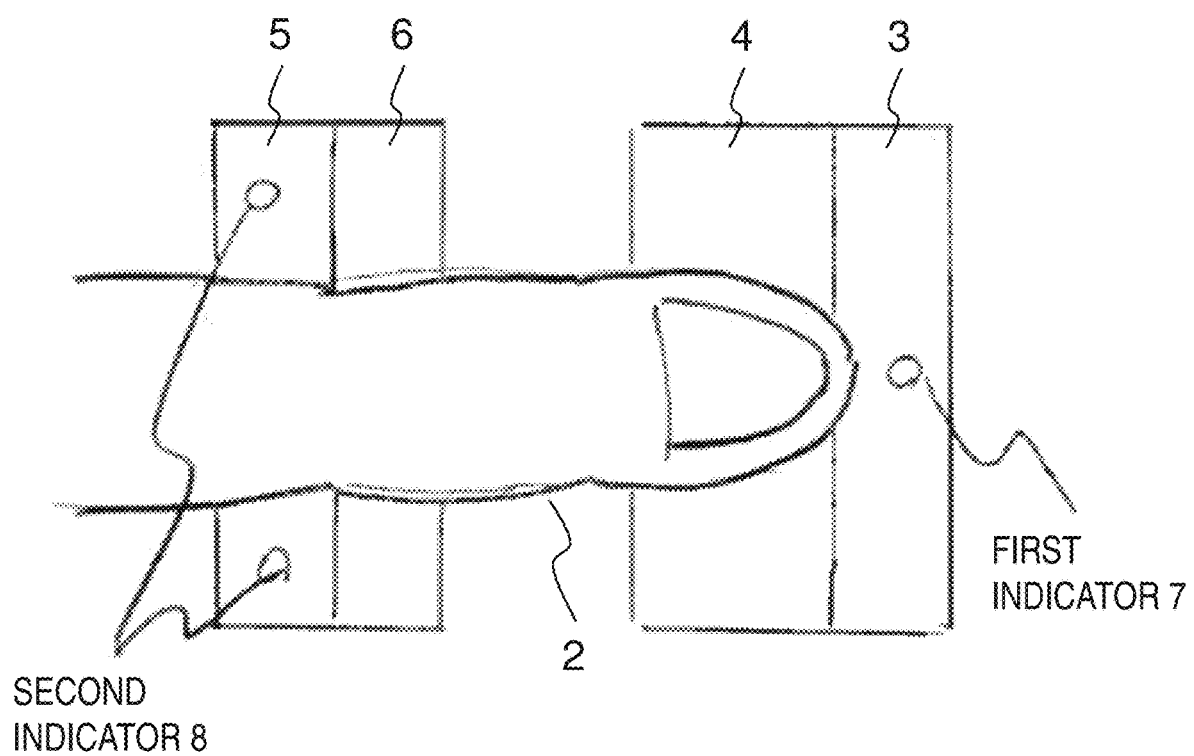
FIG. 5 is a top view of an example showing a configuration and layout of the placement unit and a display unit in the biometric imaging device according to the first and second exemplary embodiments.

FIG. 5 is a top view of an example showing a configuration and layout of the placement unit 15 and the display unit 21 in the biometric imaging device 14. Referring to FIG. 5, the first indicator 7 is arranged at the fingertip region of the first finger guide 3, and as described later, communicates to the operator at appropriate timing so that the fingertip region is correctly placed. Meanwhile, the second indicators 8 are arranged on the two sides of the second finger guide 5 (two units are shown as an example), and as described later, communicate to the operator at appropriate timing so that the finger base region is correctly placed. It is to be noted that the number of units of the first indicator 7 and the second indicators 8 and the layout are merely exemplary, and the configuration of the indicators of the present invention is not limited to modes shown in the drawings.

The determining unit 17 determines whether or not the finger 2 is placed on the placement unit 15, based on whether or not a feature of the finger 2 (for example, veins of the finger 2, a profile of the finger 2, or the like) has changed in image(s) taken by the camera 1.

In a case where it is determined that the finger 2 has been placed on the placement unit 15, the authentication unit 18 performs personal authentication based on at least one of: veins or fingerprint of the finger 2 that is included in an image.

The determining unit 17 and the authentication unit 18 may be implemented in a computer configured with a microprocessor, memory and the like, connected to the camera 1 and the display unit 21. It is to be noted that although not shown in the drawings, the biometric imaging device 14 may be further provided with an image processing unit and a database. The image processing unit performs image processing of a highlighted fingerprint or vein image of the finger 2 as appropriate. The database records measured data and presents the recorded measured data for collation.

The light source 22 is preferably a light source of wavelength 650 to 900 nm by which hemoglobin absorption can be observed. The first transparent plate 4 and the second transparent plate 6 may be such that they transmit the wavelength of light radiated by the light source 22. It is to be noted that if light from the light source 22 is radiated from below (the camera 1 side in FIG. 4), it is possible to obtain a reflected light image of veins and a fingerprint image at the same time. Meanwhile, by radiating light from the light source 22 from above (above the finger 2 in FIG. 4), a clearer transmitted light image of the veins is observed.

Next, a description is given of operations of the biometric imaging device 14 shown in FIG. 3 to FIG. 5.

First, when preparations are completed for biometric authentication in a state where the finger 2 is not placed, the first indicator 7 and the second indicators 8 flash so as to prompt the action of placing the finger 2.

If the finger 2 comes into contact with the first transparent plate 4 or the second transparent plate 6, the veins are under pressure and blood flow is obstructed. The camera 1 takes images before and after the finger 2 makes contact with the first transparent plate 4 and the second transparent plate 6, and transmits the images taken to the determining unit 17. The determining unit 17 determines whether the finger 2 is in contact with the first transparent plate 4 and the second transparent plate 6, based on a change in blood flow contained in the image.

The following method may be used with regard to timing of taking an image of the finger 2 by the camera 1. The camera 1 may start taking a video at timing at which the operator is prompted to perform an operation, by guidance of a display device (display) not shown in the drawings or the abovementioned display unit 21 (a lamp or the like). Meanwhile, the image taken by the camera 1 may be confirmed by the determining unit 17, and a video recording may be started at timing at which the image changes when the finger 2 arrives at the biometric imaging device 14. Next, if the image becomes stable (that is, the image is no longer changing), taking images by the camera 1 is stopped. The biometric imaging device 14 stores two images taken just before the image becomes stable and when it is stable. It is to be noted that upon determining the timing for taking an image, the profile of the finger 2 may also be used as a determination material. For example, during the image is stable, in a case where the image does not include such a profile that is determinable as a finger, imaging need not be performed.

Figure 6:
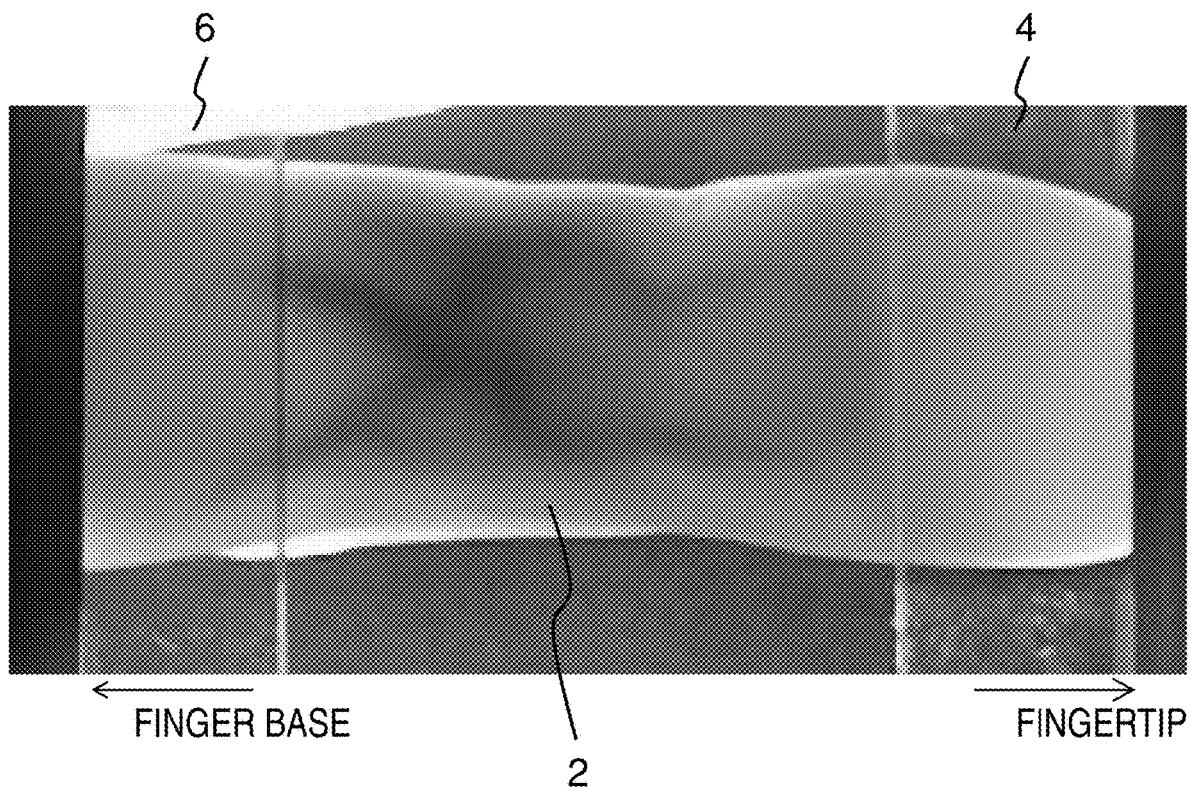
FIG. 6 is a view showing an example of an image taken by the biometric imaging device according to the first and second exemplary embodiments.

FIG. 6 shows an example of an image taken by the camera 1 of the biometric imaging device 14, before the finger 2 makes contact with the first transparent plate 4 and the second transparent plate 6. At this instance, since the finger 2 is not in contact with the first transparent plate 4 and the second transparent plate 6, blood flow at the fingertip region and the finger base region is not obstructed. Referring to FIG. 6, clear veins are observed at any of the fingertip region on the first transparent plate 4 and the finger base region on the second transparent plate 6.

Figure 7:
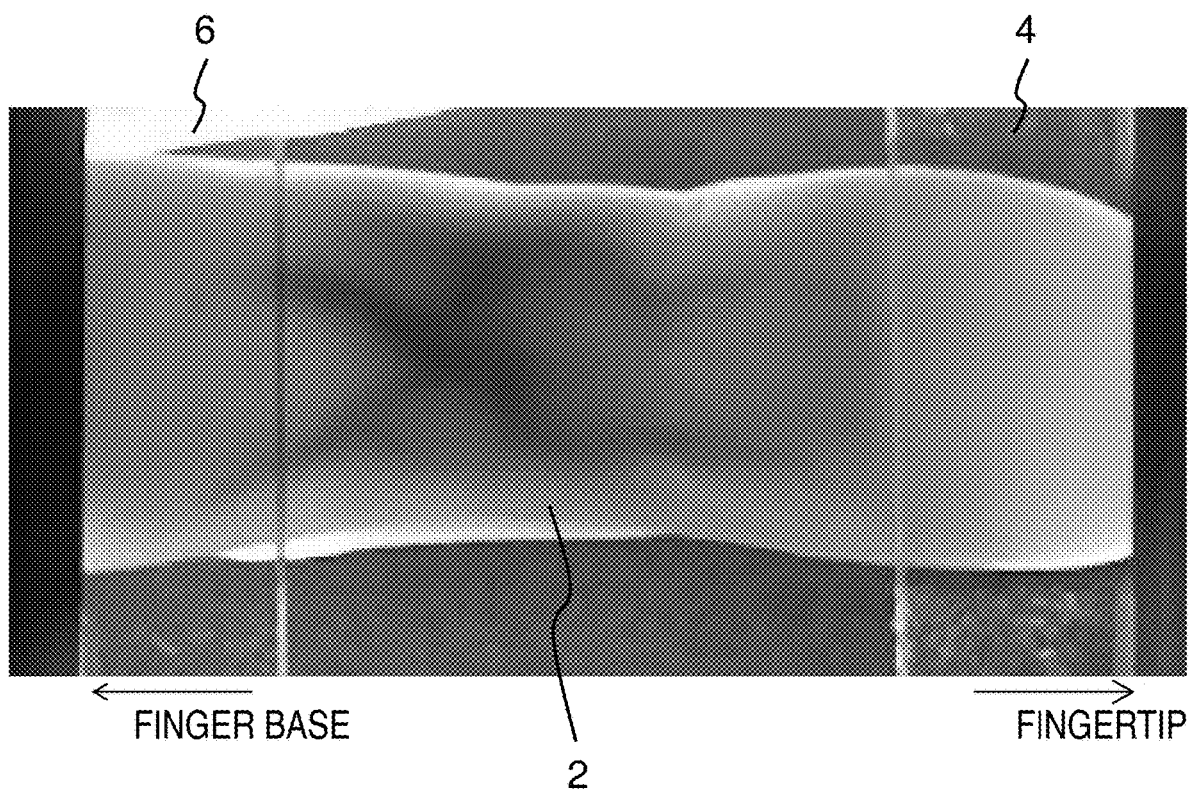
FIG. 7 is a view showing an example of an image taken by the biometric imaging device according to the first and second exemplary embodiments.

FIG. 7 shows an example of an image taken by the camera 1 of the biometric imaging device 14, after the finger 2 makes contact with the first transparent plate 4 and the second transparent plate 6. At this instance, since the finger 2 is in contact with the first transparent plate 4 and the second transparent plate 6, veins in the fingertip region and the finger base region of the finger 2 is under pressure and blood flow is obstructed. Referring to FIG. 7, all vein images or a portion thereof disappear at any of the fingertip region on the first transparent plate 4 and the finger base region on the second transparent plate 6.

By blood flow decreasing or stopping due to pressure being applied, a portion or all of vein images disappear in the images taken by the camera 1. The determining unit 17, as an example, can detect a change in the blood flow based on a change in the number of pixels recognized as corresponding to veins. For example, by taking the difference in patterns corresponding to veins, in images before and after applying pressure as shown in FIG. 6 and FIG. 7, the determining unit 17 can comprehend that the blood flow has changed.

On determining that both the fingertip region and the finger base region of the finger 2 are placed on the placement unit 15, the determining unit 17 instructs the camera 1 to obtain an image(s) for authentication. The authentication unit 18 performs personal authentication based on the image(s) for authentication that has been obtained. Here, the authentication unit 18 performs personal authentication based on at least one of veins or fingerprint of the finger 2 included in the image for authentication.

After obtaining the image for authentication, the determining unit 17 checks the vein image, and if the finger 2 is still placed on the placement unit, turns off the first indicator 7 and the second indicators 8. Thus, the operator is informed that an image has been correctly inputted, and is prompted to remove his/her hand 2 from the placement unit 15.

Meanwhile, in a case where there is no change in vein image on the first transparent plate 4 and it is determined that the fingertip region is not in contact, the determining unit 17 prompts the operator to put the fingertip region in contact, by flashing the first indicator 7.

Meanwhile, in a case where there is no change in vein image on the second transparent plate 6 and it is determined that the finger base region is not in contact, the determining unit 17 prompts the operator to lower the finger base region and put the finger in contact, by flashing the second indicators 8.

Furthermore, in a case where no change can be detected in either of the vein image on the first transparent plate 4 and the vein image on the second transparent plate 6, the determining unit 17 prompts the operator to put the finger 2 in contact, by flashing both the first indicator 7 and the second indicators 8.

According to the biometric imaging device 14 of the present exemplary embodiment, by providing the first and second finger guides 3 and 5, and the first and second transparent plates 4 and 6, for a fingerprint and vein reading device in a non-contact state, it is possible to communicate to the operator a correct placing action in which the finger 2 is not in floating. In addition, according to the biometric imaging device 14 of the present exemplary embodiment, by detecting placement of the finger 2 based only on an image change, it becomes unnecessary to provide a touch sensor for detecting finger contact as in Patent Literature 5.

It is to be noted that consideration may also be given to observing the disappearance of veins according to the first and second finger guides 3 and 5 only, without providing the first and second transparent plates 4 and 6. However, in a case where transparent plates are not provided, unless a large pressure is applied there is a risk of a noticeable difference not being observable in images before and after the finger 2 is placed. For example, even in a case where contact by the finger 2 is detected by a touch sensor, if there would be no transparent plate, change in finger image may be poor (or weak) and such a case may happen where a determination is difficult with regard to placement of the finger 2 and whether the finger is fake or not. On the other hand, when a transparent plate is provided, even in a case where placing is done with a relatively small force, it is possible to observe a vein change in images before and after placing. That is, by providing the first and second transparent plates 4 and 6, it is possible to detect placing of the finger 2 with high accuracy, and to render a touch sensor unnecessary.

In the present exemplary embodiment, by providing the first and second finger guides 3 and 5, the first and second transparent plates 4 and 6, and the first and second indicators 7 and 8, relative to the non-contact fingerprint and vein reading biometric imaging device 14, it is possible to visually communicate to the operator such a correct placing action that the finger 2 is in contact. That is, by providing the first and second finger guides 3 and 5, the first and second transparent plates 4 and 6, and the first and second indicators 7 and 8, and giving an appropriate display at appropriate timing during operation when a user's finger 2 is placed on the device, it is possible to realize high biometric authentication accuracy by preventing image deterioration due to the finger 2 floating (i.e., not being in contact).

Additionally, according to the biometric imaging device 14, by using a specific biometric change according to a profile or vein pressure of the finger 2 when the finger 2 comes into contact with the first and second transparent plates 4 and 6 provided on the first and second finger guides 3 and 5, and analyzing profile images and vein images of the finger 2, it is possible to distinguish a fake finger and a real finger with a higher degree of accuracy. For example, by comparing the finger profile and vein images before and after contact with a guide for finger images near a fingerprint region of a fingertip region, and observing change therein, it is possible to recognize a fake finger (replica) with a higher degree of accuracy. In this way, when performing biometric authentication, it is possible to prevent malicious "impersonation".

Thus, according to the biometric imaging device 14 of the present exemplary embodiment, when images of a fingerprint pattern and a vein pattern of the finger are inputted simultaneously to a biometric feature image input device for authenticating a person, it is possible to realize high biometric authentication accuracy by preventing image deterioration caused by finger floatation (deviation) from, a suitable image-taking position, and to realize high impersonation prevention functionality using change of biometric features when the finger is in contact. Specifically, by providing the transparent plates and the indicators for the finger guides, and making an appropriate display at appropriate timing when a user places a finger on the device, it is possible to realize high biometric authentication accuracy by preventing image deterioration due to the finger floating away from a suitable imaging position. Additionally, by using a change in a biometric feature according to the finger profile or vein pressure when the finger is in contact with the finger guides, and analyzing the profile images and vein images of the finger, it is possible to realize highly accurate biometric authentication and also to easily distinguish a fake (replica) finger and a real finger.

Second Exemplary Embodiment

Next, a description is given concerning a biometric imaging device according to a second exemplary embodiment, making reference to the drawings. A configuration of the biometric imaging device 14 of the present exemplary embodiment is similar to the configuration of the biometric imaging device according to the first exemplary embodiment shown in FIG. 3 to FIG. 5. A description given below is centered on differences between the biometric imaging device 14 of the present exemplary embodiment and the biometric imaging device of the first exemplary embodiment.

In the biometric imaging device of the first exemplary embodiment the determining unit 17 determines whether or not a finger 2 is placed on the placement unit 15 based on whether or not a feature of the finger 2 (for example, veins of the finger 2, profile of the finger 2, or the like) has changed in images taken by the camera 1. On the other hand, in the biometric imaging device of the present exemplary embodiment the determining unit 17 determines whether or not the finger 2 is placed on the placement unit 15 based on difference in a feature of the finger 2 (for example, veins of the finger 2, a profile of the finger 2, or the like) at a place where the finger 2 and the placement unit 15 are in contact and a place where they are not in contact.

In a case of using the veins of the finger 2 as a feature of the finger 2 at a place (or portion) where the finger 2 and the placement unit 15 are in contact and a place (or portion) where they are not in contact, the determining unit 17 can use vein continuity at both places. The boundary between a place at which the finger 2 and first and second transparent plates 4 and 6, provided in the placement unit 15, are in contact, and a place where they are not in contact is known in advance. Therefore, in a case where there is a vein interruption near this boundary, the determining unit 17 can determine that the finger 2 is in contact with the placement unit 15.

On the other hand, the determining unit 17 can use the profile of the finger 2 as a feature of the finger 2 at a place where the finger 2 and the placement unit 15 are in contact and a place where they are not in contact. This is because, since the finger 2 has elasticity, it becomes wider at the place of contact than at the place of non-contact. In actuality, it is known that the finger 2 tends to become easily wider between the second joint and the third joint, and if in contact, the change in the width of the finger 2 is particularly clearly observed at the finger base side. In the determining unit 17, the boundary between a place at which the finger 2 and the first and second transparent plates 4 and 6, provided in the placement unit 15, are in contact, and a place where they are not in contact is known in advance. Therefore, the determining unit 17 can determine whether or not the finger 2 is in contact with the placement unit 15, based on difference in the profile (width) of the finger 2 at (between) the two places.

FIG. 6 shows an example of an image taken by the camera 1 of the biometric imaging device 14, before the finger 2 makes contact with the first transparent plate 4 and the second transparent plate 6. First, a description is given of a case of using veins of the finger 2 as a feature when determining placing of the finger 2. Since the finger 2 is not in contact with the first transparent plate 4 and the second transparent plate 6, blood flow at the fingertip region and the finger base region of the finger 2 is not obstructed. Referring to FIG. 6, since there is no vein interruption near the boundaries (2 places) of the place where the first and the second transparent plates 4 and 6 and the finger 2 are in contact and the place where they are not in contact, the determining unit 17 determines that the finger 2 is not in contact with the placement unit 15.

Next, a description is given of a case of using the profile (width) of the finger 2 as a feature when determining placing of the finger 2. Referring to FIG. 6, since the finger 2 is not in contact with the first transparent plate 4 and the second transparent plate 6, the width of the fingertip region and the finger base region of the finger 2 do not notably change at the 2 places: the place of contact and the place of non-contact. Therefore, the determining unit 17 determines that the finger 2 is not in contact with the placement unit 15.

FIG. 7 shows an example of an image taken by the camera 1 of the biometric imaging device 14, after the finger 2 made contact with the first transparent plate 4 and the second transparent plate 6. First, a description is given of a case of using veins of the finger 2 as a feature when determining placing of the finger 2. Since the finger 2 is not in contact with the first transparent plate 4 and the second transparent plate 6, veins at the fingertip region and the finger base region of the finger 2 are not under pressure, and blood flow is not obstructed. Referring to FIG. 7, there is a vein interruption near the boundaries (2 places): the place where the first and the second transparent plates 4 and 6 and the finger 2 are in contact, and the place where they are not in contact. Therefore, the determining unit 17 determines that the finger 2 is in contact with the placement unit 15.

Next, a description is given of a case of using the profile (width) of the finger 2 as a feature when determining placing of the finger 2. Referring to FIG. 7, since the finger 2 is in contact with the first transparent plate 4 and the second transparent plate 6, the width of the fingertip region and the finger base region of the finger 2 are wider at a place of contact in comparison to a place of non-contact. In particular, the width of the finger 2 is noticeably larger at the place where the second transparent plate 6 and the finger base region of the finger 2 are in contact, in comparison to a place where they are not in contact. At this time, the determining unit 17 determines that the finger 2 is in contact with the placement unit 15.

According to the biometric imaging device 14 of the present exemplary embodiment an effect is realized that is similar to the biometric imaging device of the first exemplary embodiment. Furthermore, with the biometric imaging device 14 of the present exemplary embodiment, by using a biometric feature difference between a place of contact and a place of non-contact, the following type of beneficial effect is obtained, in comparison with the biometric imaging device of the first exemplary embodiment (where use is made of biometric feature difference before and after contact). That is, according to the biometric imaging device 14 of the present exemplary embodiment, since it is possible to determine whether or not the finger is placed based on images of only where there is contact, even with a scanner method in which continuous video capture is difficult (for example, a case where it is not possible to obtain a video due to resolution priority), it is possible to determine whether the biometric object is placed on the placement unit 15.

Third Exemplary Embodiment

Figure 8:
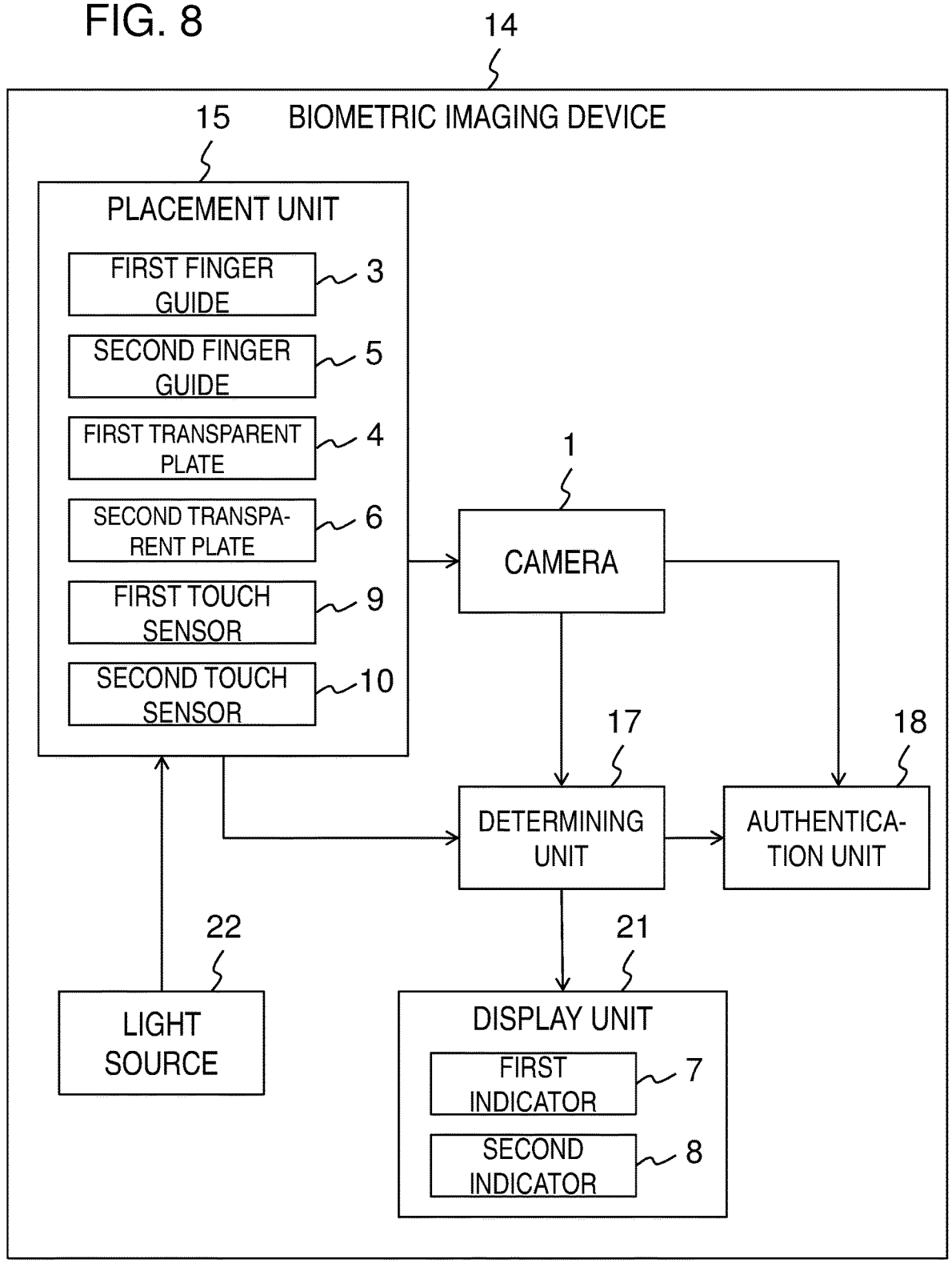
FIG. 8 is a block diagram showing an example of a configuration of the biometric imaging device according to a third exemplary embodiment.

Next, a description is given concerning a biometric imaging device according to a third exemplary embodiment, making reference to the drawings. FIG. 8 is a block diagram showing an example of a configuration of the biometric imaging device 14 according to the present exemplary embodiment. The biometric imaging device 14 of the present exemplary embodiment differs from the biometric imaging device 14 (FIG. 3) of the first and second exemplary embodiments in the point that the placement unit 15 additionally has a first touch sensor 9 and a second touch sensor 10. With regard to the other points, the biometric imaging device 14 of the present exemplary embodiment has a configuration similar to the biometric imaging device 14 of the first and second exemplary embodiments. It is to be noted that in the biometric imaging device 14 of the present exemplary embodiment, first and second transparent plates 4 and 6 may be provided or may be omitted.

FIG. 9 is a front view of an example showing a configuration and layout of a camera 1 and a placement unit 15 of the biometric imaging device 14. Referring to FIG. 9, a first finger guide 3 has the first transparent plate 4 that a fingerprint of a finger 2 comes into contact with, and a first touch sensor 9 that detects contact by the fingerprint of the finger 2. Meanwhile, the second finger guide 5 has a second transparent plate 6 that a finger base region of the finger 2 comes into contact with, and a second touch sensor 10 that detects contact by the finger base region of the finger 2.

Figure 10:
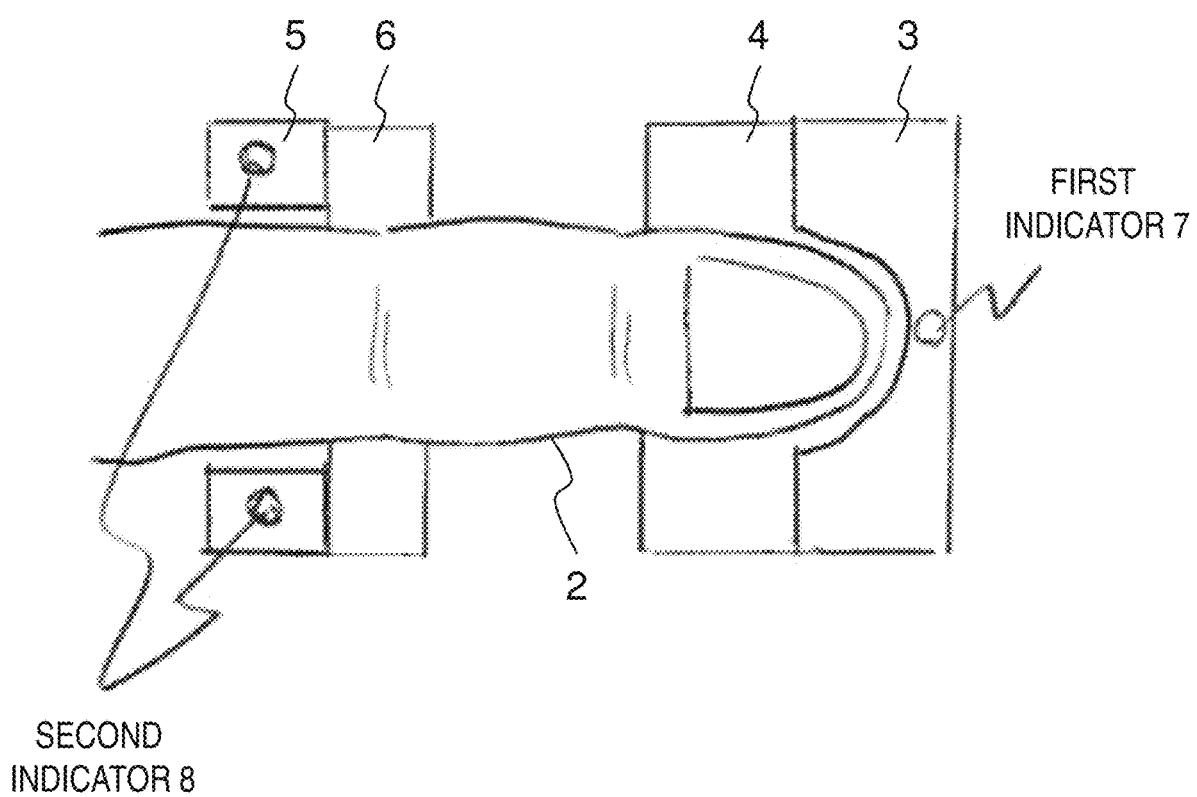
FIG. 10 is a top view of an example showing a layout of a placement unit and a display unit in the biometric imaging device according to the third exemplary embodiment.

FIG. 10 is a top view of an example showing a configuration and layout of the placement unit 15 and a display unit 21 in the biometric imaging device 14. Referring to FIG. 10, a first indicator 7 is placed at a fingertip region of the first finger guide 3, and as described later, communicates with an operator at appropriate timing so that the fingertip region is correctly placed. Meanwhile, second indicators 8 are placed on the two sides of the second finger guide 5 (two units are shown as an example), and as described later, communicate to the operator at appropriate timing so that the finger base region is correctly placed.

The determining unit 17 determines whether or not the finger 2 is placed on the placement unit 15, based on whether or not a feature of the finger 2 (for example, veins of the finger 2, profile of the finger 2, or the like) has changed in images taken by the camera 1, and whether or not contact has been detected by the first and second touch sensors 9 and 10.

Next, a description is given of operations of the biometric imaging device 14 shown in FIG. 8 to FIG. 10.

First, when preparations are completed for biometric authentication in a state where the finger 2 is not placed, the first indicator 7 and the second indicators 8 flash to prompt an operator to place his/her finger 2.

If the finger 2 is in contact with the first transparent plate 4 or the second transparent plate 6, the veins are under pressure and blood flow is obstructed. The camera 1 takes images before and after the finger 2 makes contact with the first transparent plate 4 and the second transparent plate 6, and transmits the images taken to the determining unit 17.

It is to be noted that in a case where the first transparent plate 4 and the second transparent plate 6 are not provided, if the finger 2 is in contact with the first touch sensor 9 on the first finger guide 3 or the second touch sensor 10 on the second finger guide 5, in the same way, the veins are under pressure and blood flow is obstructed. Therefore, in a case where the first transparent plate 4 and the second transparent plate 6 are not provided, the camera 1 takes images before and after the finger 2 is in contact with the first touch sensor 9 on the first finger guide 3 and the second touch sensor 10 on the second finger guide 5, and transmits the images taken to the determining unit 17.

Meanwhile, on detecting contact by the finger 2, the first touch sensor 9 and the second touch sensor 10 notify the determining unit 17 that contact by the finger 2 has been detected.

The determining unit 17 determines whether or not the fingertip region and the finger base region of the finger 2 are placed on the placement unit 15, based on a change of blood flow contained in the images and detection results by the first and second touch sensor 9 and 10.

Figure 11:
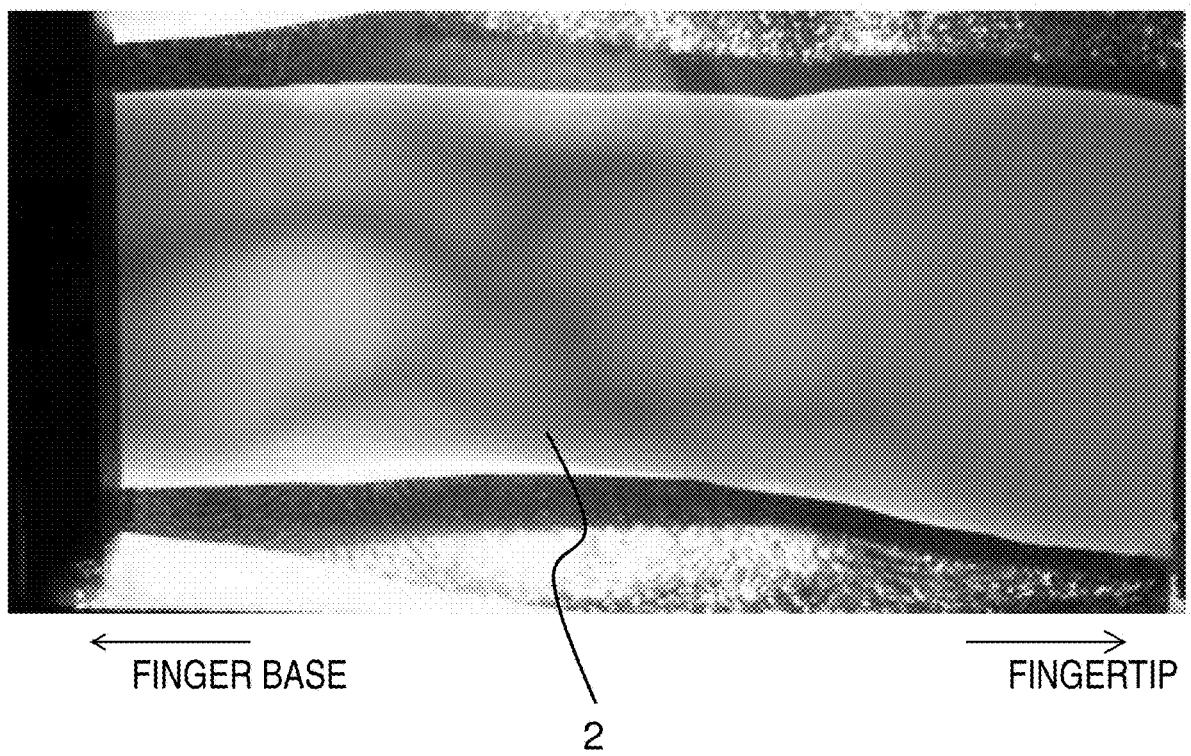
FIG. 11 is a view showing an example of an image taken by the biometric imaging device according to the third exemplary embodiment.

FIG. 11 shows an example of an image taken by the camera 1 of the biometric imaging device 14, before the finger base region of the finger 2 is placed on the second finger guide 5 of the placement unit 15. It is to be noted that FIG. 11 shows an image in a case where the first and second transparent plates 4 and 6 are not present. At this time, since the finger 2 and the second finger guide 5 are not in contact, blood flow at the finger base region of the finger 2 is not obstructed. Therefore, as shown in FIG. 11, veins are clearly observed in the finger base region.

Figure 12:
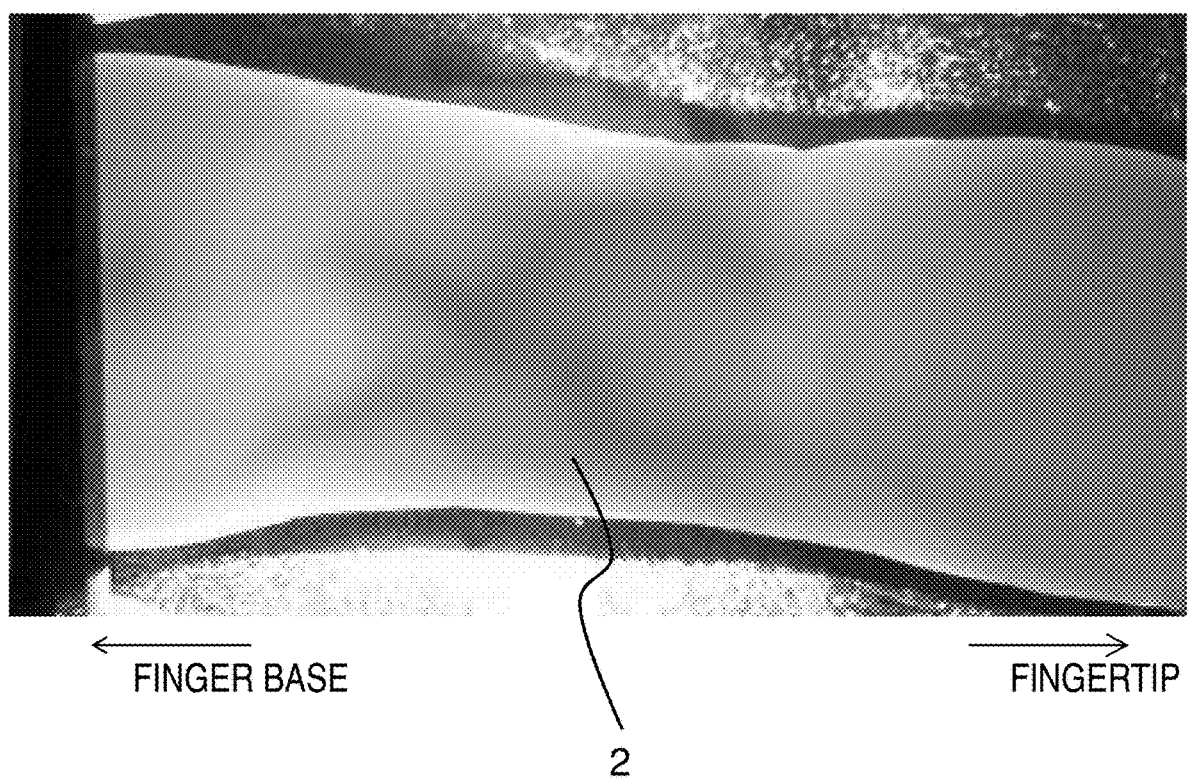
FIG. 12 is a view showing an example of an image taken by the biometric imaging device according to the third exemplary embodiment.

FIG. 12 shows an example of an image taken by the camera 1 of the biometric imaging device 14, after the finger base region of the finger 2 has been placed on the second finger guide 5 of the placement unit 15. It is to be noted that FIG. 12 shows an image in a case where the first and second transparent plates 4 and 6 are not present. At this time, the finger 2 and the second finger guide 5 are in contact, veins at the finger base region of the finger 2 are under pressure and blood flow is obstructed. Therefore, as shown in FIG. 12, all or part of the vein images disappear at the finger base region. Referring to FIG. 12, it is understood that the width of the finger base region is wider in comparison with FIG. 11.

Based on whether or not detection has been made of a change in an vein image, and/or a change in the profile of the placed finger 2, and also whether or not contact has been detected by the first and second touch sensors 9 and 10, the determining unit 17 determines whether or not the finger has been placed and determines whether the placed finger 2 is a biological object or a replica. In a case of using a vein image change, the determining unit 17 uses a change in vein images of the fingertip region and/or the finger base region that is pressurized by the first or second finger guides 3 and 5. Meanwhile, in a case of using an image change of the profile of the finger 2, the determining unit 17 uses the fact that, due to the finger 2 being elastic, the fingertip region and the finger base region respectively make contact with the first and second finger guides 3 and 5, pressure is applied, and the finger image becomes wider. Specifically, after contact has been made, an observation is made that the finger base region and the profile of the finger base region have become wider, and that the vein image has been partially damaged due to a change in blood flow due to pressure being applied.

Two images, before and after placing, are compared, and if there are changes in both blood flow and profile, the determining unit 17 can determine that the finger 2 is not a fake finger (replica) but comes from a biological object. This is because in a case where a replica is formed from flexible resin or the like and it is not possible to distinguish a biological object and a replica with only a change in profile, there would be no change in vein images of the replica before and after placing.

On determining that both the fingertip region and the finger base region of the finger 2 are placed on the placement unit 15, the determining unit 17 instructs the camera 1 to obtain an image for authentication.

The authentication unit 18 performs personal authentication based on the obtained image for authentication. Here, the authentication unit 18 may perform personal authentication based on at least one of veins or fingerprint of the finger 2 included in the images for authentication.

After obtaining the images for authentication, the determining unit 17 checks the vein image, and if the finger is still placed on the placement unit, turns off the first indicator 7 and the second indicators 8. Thus, the operator is informed that an image has been correctly inputted, and is prompted to remove the finger 2 from the placement unit 15.

Meanwhile, in a case where there is no change in vein image on the first transparent plate 4, or the first touch sensor 9 does not detect contact by the fingertip region and a determination is made that the fingertip region is not in contact, the determining unit 17 prompts the operator to put the fingertip region in contact by flashing the first indicator 7.

In a case where there is no change in vein image on the second transparent plate 6, or the second touch sensor 10 does not detect contact by the fingertip region and a determination is made that the fingertip region is not in contact, the determining unit 17 prompts the operator to lower the finger base region and put the finger in contact by flashing the second indicators 8.

In a case where no change can be detected in either the image on the first transparent plate 4 or the image on the second transparent plate 6 and contact is not detected by the first or second touch sensors 9 and 10, the determining unit 17 prompts the operator to put the finger 2 in contact, by flashing both the first indicator 7 and the second indicators 8.

According to the biometric imaging device 14 of the present exemplary embodiment, by providing the first and second finger guides and 5, and the first and second touch sensors 9 and 10, for a non-contact fingerprint and vein reading device, it is possible to communicate to the operator a correct placing action in which the finger 2 is in contact. According to the biometric imaging device 14 of the present exemplary embodiment, by detecting placement of the finger 2 by both an image change and a touch sensor, it is possible to detect placement of the finger 2 more accurately, in comparison with detecting placing of the finger 2 based on only an image change or only a touch sensor. That is, according to the biometric imaging device 14 of the present exemplary embodiment, it is possible to doubly detect contact of a finger by using the image and the touch sensor together, and it is possible to improve reliability.

According to the biometric imaging device 14 of the present exemplary embodiment, it is possible to detect that the finger 2 is placed by the first and/or second touch sensors 9 and 10, and to determine whether or not the finger 2 is a replica (fake finger) according to whether or not there is a change in vein image. Specifically, irrespective of whether it is detected that "a finger is placed (is in contact)" in a detection result by the first and/or second touch sensors 9 and 10, in a case of detecting that "a finger has not been placed (no change in vein image or profile)" in detection according to a biometric image it is possible to determine that the placed finger 2 is a replica.

It is to be noted that, in a case of using a pressure sensor as the first and second touch sensors 9 and 10, by comparing degree of pressure and a change in veins, it is possible to detect placing of the finger 2 with a still greater accuracy.

Fourth Exemplary Embodiment

Figure 13:
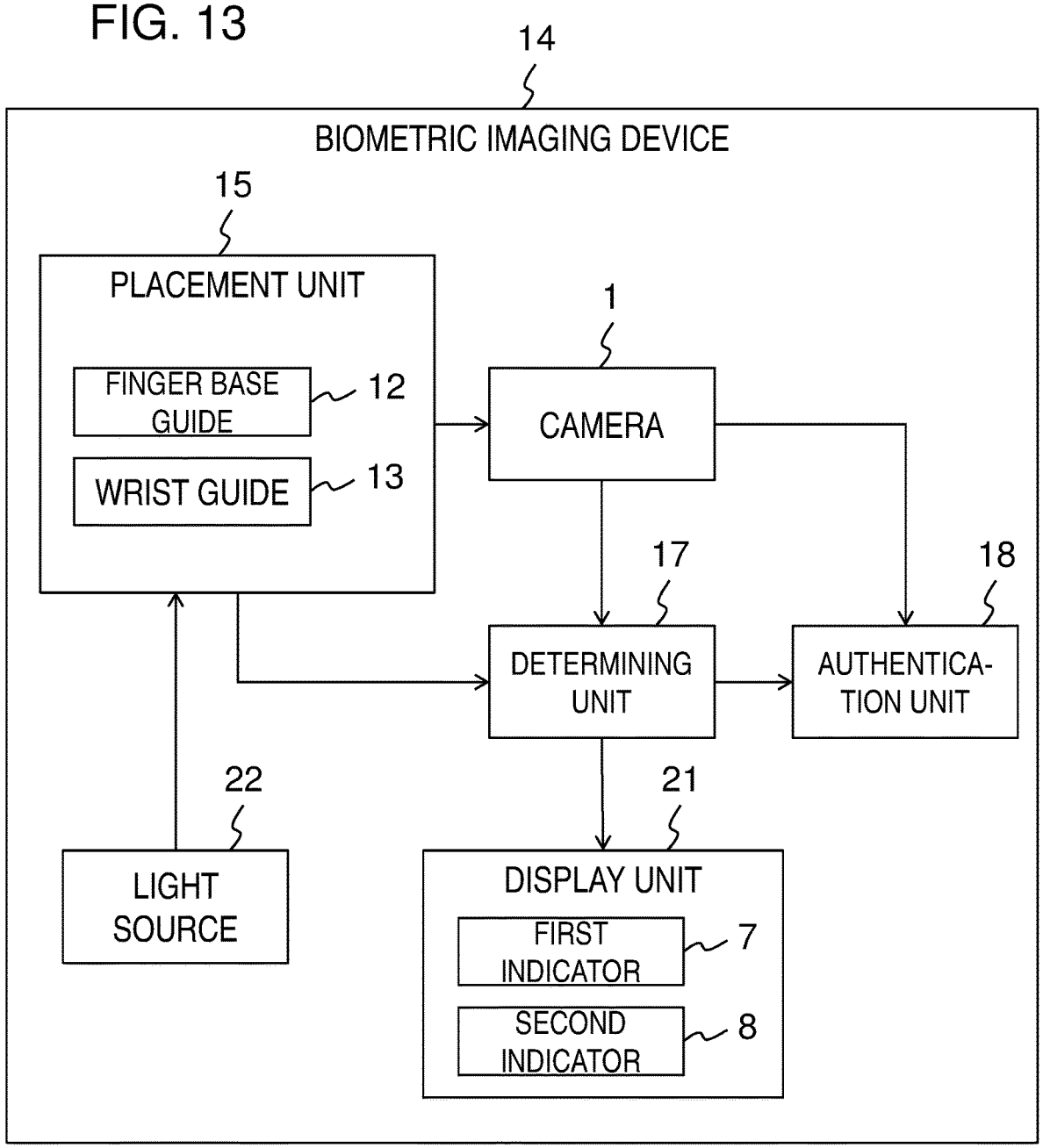
FIG. 13 is a block diagram showing an example of a configuration of the biometric imaging device according to a fourth exemplary embodiment.

Next, a description is given concerning a biometric imaging device according to a fourth exemplary embodiment, making reference to the drawings. FIG. 13 is a block diagram showing an example of a configuration of a biometric imaging device 14 according to the present exemplary embodiment. The biometric imaging device 14 of the present exemplary embodiment differs from the biometric imaging device of the first exemplary embodiment to the third exemplary embodiment in the point that the placement unit 15 has a finger base guide 12 and a wrist guide 13, instead of the first finger guide 3 and the second finger guide 5 (FIG. 3 to FIG. 5, FIG. 8 to FIG. 10). With regard to the other points, the biometric imaging device 14 of the present exemplary embodiment has a configuration similar to the biometric imaging device 14 of the first to third exemplary embodiments.

Figure 14A:
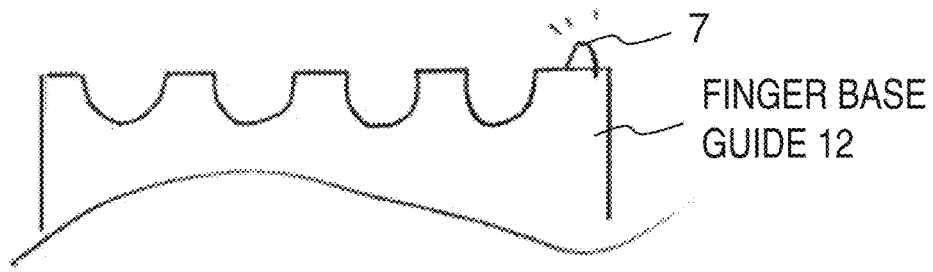
FIGS. 14A-14C are lateral views and a top view showing an example of a configuration of a placement unit in the biometric imaging device according to the fourth exemplary embodiment.

FIG. 14A is a front view of an example showing a configuration of a placement unit 15 of the biometric imaging device 14. Referring to FIG. 14A, the finger base guide 12 is a guide to support a finger base region. It is to be noted that the finger base guide 12 may have a transparent plate that the finger base region makes contact with. A touch sensor to detect contact by the finger base region may be provided on the finger base guide 12.

Figure 14B:
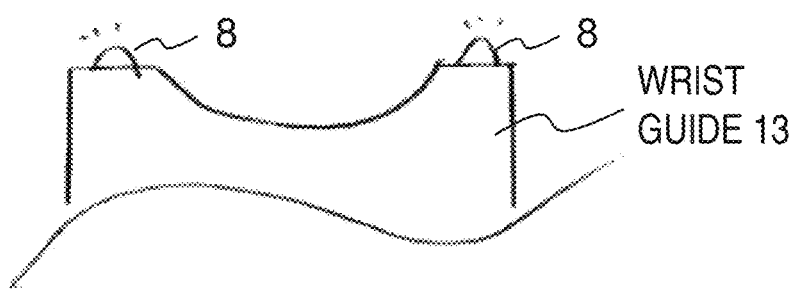

FIG. 14B is a side view of an example showing a configuration of the placement unit 15 of the biometric imaging device 14. Referring to FIG. 14B, the wrist guide 13 is a guide to support a wrist region. It is to be noted that the wrist guide 13 may have a transparent plate that the wrist region makes contact with. A touch sensor to detect contact by the wrist region may be provided on the wrist guide 13.

Figure 14C:
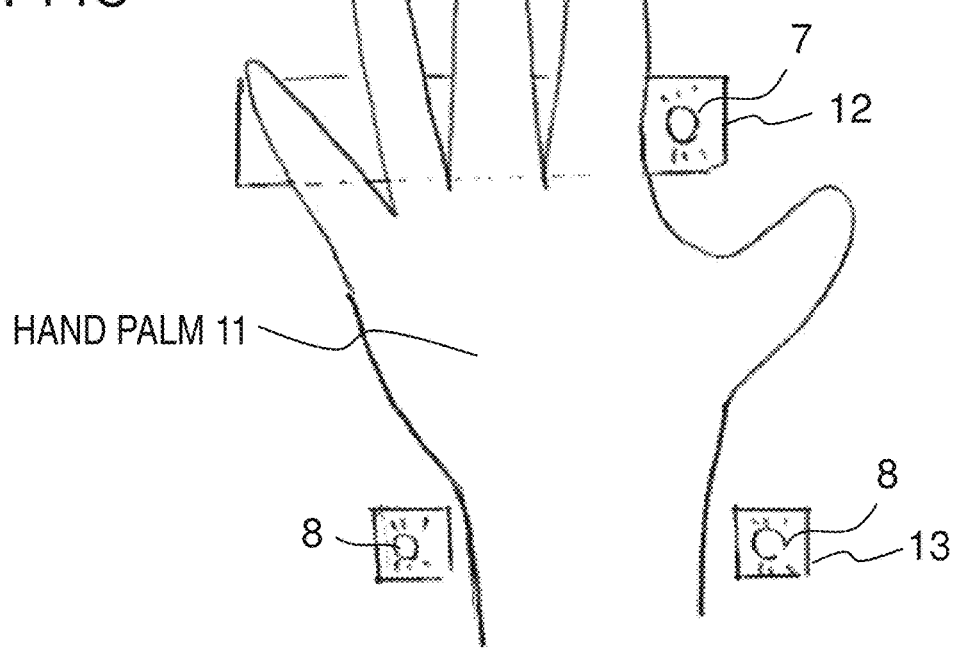

FIG. 14C is a top view of an example showing a configuration and layout of the placement unit 15 and a display unit 21 in the biometric imaging device 14. Referring to FIG. 14C, a first indicator 7 is arranged on the finger base guide 12, and as described later, communicates to an operator at appropriate timing so as to correctly place the finger base region. Meanwhile, second indicators 8 are arranged on each side of a place where the wrist region is placed on the wrist guide 13 (2 units are shown as an example), and as described later, communicate to the operator at appropriate timing so as to correctly place the wrist region.

The determining unit 17 determines whether or not a hand palm 11 is placed on the placement unit 15, based on whether or not a feature of the hand palm 11 (for example, veins of the palm 11, profile of the palm 11, or the like) has changed in images taken by a camera 1.

In a case where it is determined that the hand palm 11 is placed on the placement unit 15, an authentication unit 18 performs personal authentication based at least one of veins and a palm print of the hand palm 11, contained in an image.

The determining unit 17 and the authentication unit 18 may be implemented in a computer configured with a microprocessor, memory and the like, connected to the camera 1 and the display unit 21.

Next, a description is given of operations of the biometric imaging device 14 shown in FIG. 13 and FIGS. 14A-14C.

First, when preparations are completed for biometric authentication in a state in which the hand palm 11 is not placed, the first indicator 7 and the second indicators 8 flash to prompt the operator to place his/her hand palm 11.

When the hand palm 11 makes contact with the finger base guide 12 or the wrist guide 13, the vein is pressed and blood flow is obstructed, and the profile of the hand palm 11 changes. The camera 1 takes images before and after the hand palm 11 makes contact with the finger base guide 12 and the wrist guide 13, and transmits the images taken to the determining unit 17.

The determining unit 17 determines whether the hand palm 11 is in contact with the finger base guide 12 and the wrist guide 13, based on a change in blood flow contained in the images, and/or a change in the profile of the hand palm 11. On determining that both the finger base region and the wrist region of the hand palm 11 are placed on the placement unit 15, the determining unit 17 instructs the camera 1 to obtain an image for authentication.

The authentication unit 18 performs personal authentication based on the obtained image for authentication. Here, the authentication unit 18 may perform personal authentication based on at least one of veins and palm print of the hand palm 11 included in the image for authentication.

After obtaining the image for authentication, the determining unit 17 checks a feature (for example veins, profile or the like) of the hand palm 11 in the image, and if the hand palm 11 is still placed on the placement unit, turns off the first indicator 7 and the second indicators 8. Thus, the operator is informed that an image has been correctly inputted, and the operator is prompted to remove his/her hand palm 11 from the placement unit 15.

Meanwhile, in a case where there is no change in the feature of the hand palm 11 in the image close to the finger base guide 12 and it is determined that the finger base region is not in contact, the determining unit 17 prompts the operator to put the finger base region in contact by flashing the first indicator 7.

In a case where there is no change in the feature of the hand palm 11 in the image close to the wrist guide 13, and it is determined that the wrist region is not in contact, the determining unit 17 prompts the operator to lower his/her wrist region to make contact, by flashing the second indicators 8.

Furthermore, in a case where no change can be detected in the feature of the hand palm 11 in either of the image near the finger base guide 12 and the image near the wrist guide 13, the determining unit 17 prompts the operator to put his/her hand palm in contact by flashing both the first indicator 7 and the second indicators 8.

According to the biometric imaging device 14 of the present exemplary embodiment, by providing the finger base guide 12 and the wrist guide 13, and the first and second indicators 7 and 8, for a non-contact palm print and vein reading device, it is possible to instruct the operator regarding a correct placing action in which the hand palm 11 is in contact. According to the biometric imaging device 14 of the present exemplary embodiment, by detecting placement of the hand palm 11 based only on a change in a feature of the hand palm 11 included in an image, it is unnecessary to provide a touch sensor for detecting contact as in Patent Literature 5.

It is to be noted that in the present exemplary embodiment, a transparent plate may be provided similar to the first exemplary embodiment. By providing the transparent plate, a noticeable difference occurs in images before and after the hand palm 11 is placed, even without pressing the finger base guide 12 and the wrist guide 13 with a large force, and it is possible to determine whether or not the hand palm 11 is placed, by the determining unit 17.

It is to be noted that in the present exemplary embodiment, a touch sensor may be provided similar to the third exemplary embodiment. By detecting placement of the hand palm 11 by both image change and touch sensor, it is possible to detect placement of the hand palm 11 more accurately, in comparison with a case of detecting placement of the hand palm 11 based on only the image change or only the touch sensor.

In a case of providing the touch sensor, it is possible to detect by the touch sensor that the hand palm 11 has been placed, and to determine whether or not the hand palm 11 is a replica according to whether or not there is a change in a vein image. Specifically, irrespective of whether it has been detected that "a palm has been placed (is in contact)" in a detection result by the touch sensor, in a case of detecting that "a palm has not been placed (no change in vein image or profile)" in detection according to a biometric image, it is possible to determine that the hand palm 11 that has been placed is a replica (fake biological object).

It is to be noted that the following modes are possible in the present invention.

<First Mode>

As in the biometric imaging device according to the first aspect described above.

<Second Mode>

The determining unit may determine whether or not the biological object is placed on the placement unit, based on time variation of a feature of the biological object at a place where the placement unit and the biological object are in contact, in the image(s).

<Third Mode>

The determining unit may determine whether or not the biological object is placed on the placement unit, based on a comparison of a feature of the biological object at a place where the placement unit and the biological object are in contact, and a feature of the biological object at a place where the placement unit and the biological object are not in contact, in the image(s).

<Fourth Mode>

The feature of the biological object is a profile of the biological object and/or veins of the biological object, and the determining unit may determine that the biological object is placed on the placement unit, in a case where the width of the profile of the biological object has become large, and/or a case where all or part of the veins in the biological object has disappeared, in the image(s).

<Fifth Mode>

The feature of the biological object is veins of the biological object, and the determining unit may determine that the biological object is placed on the placement unit, in a case where all or part of the veins of the biological object has disappeared at a place where the placement unit and the biological object are in contact, in the image(s).

<Sixth Mode>

The feature of the biological object is a profile of the biological object, and the determining unit may determine that the biological object is placed on the placement unit, in a case where the width of the profile of 1080 the biological object has become large at a place where the placement unit and the biological object are in contact, in the image(s).

<Seventh Mode>

The placement unit has a touch sensor that detects contact by the biological object, and the determining unit may determine whether or not the biological object is a fake biological object, based on an image of the biological object and an output result of the touch sensor.

<Eighth Mode>

The biometric imaging device may be provided with a display unit for making a display to prompt that the biological object be placed on the placement unit, in a case where the biometric imaging device determines that the biological object is not placed on the placement unit.

<Ninth Mode>

As in the biometric imaging method according to the second aspect described above.

<Tenth Mode>

In the biometric imaging method, a determination may be made as to whether or not the biological object is placed on the placement unit, based on time variation of a feature of the biological object at a place where the placement unit and the biological object are in contact, in the image(s).

<Eleventh Mode>

In the biometric imaging method, a determination may be made as to whether or not the biological object is placed on the placement unit, based on a comparison of a feature of the biological object at a place where the placement unit and the biological object are in contact, and a feature of the biological object at a place where the placement unit and the biological object are not in contact, in the image(s).

<Twelfth Mode>

In the biometric imaging method, a feature of the biological object is a profile of the biological object and/or veins of the biological object, and a determination may be made as to whether or not the biological object is placed on the placement unit, in a case where the width of the profile of the biological object has become large, and/or a case where all or part of the veins in the biological object has disappeared, in the image(s).

<Thirteenth Mode>

In the biometric imaging method, a feature of the biological object are veins of the biological object, and a determination may be made that the biological object is placed on the placement unit, in a case where all or part of the veins of the biological object has disappeared at a place where the placement unit and the biological object are in contact, in the image(s).

<Fourteenth Mode>

In the biometric imaging method, a feature of the biological object is a profile of the biological object, and a determination may be made that the biological object is placed on the placement unit, in a case where the width of the profile of the biological object has become large at a place where the placement unit and the biological object are in contact, in the image(s).

<Fifteenth Mode>

The biometric imaging method may include detecting, by a touch sensor, contact by the biological object, and determining whether or not the biological object is a fake biological object based on an image of the 1135 biological object and an output result of the touch sensor.

<Sixteenth Mode>

The biometric imaging method may include making a display to prompt that the biological object be placed on the placement unit, in a case where the biological object is not placed on the placement unit.

<Seventeenth Mode>

As in the program according to the third aspect described above.

It is to be noted that the entire disclosed content of the abovementioned Patent Literature is incorporated herein by reference thereto. Modifications and adjustments of exemplary embodiments are possible within the bounds of the entire disclosure (including the scope of the claims) of the present invention, and also based on fundamental technological concepts thereof. Furthermore, various combinations and selections of various disclosed elements (including respective elements of the respective claims, respective elements of the respective exemplary embodiments, respective elements of the respective drawings, and the like) are possible within the scope of the entire disclosure of the present invention. That is, the present invention clearly includes every type of transformation and modification that a person skilled in the art can realize according to the entire disclosure including the scope of the claims and to technological concepts thereof. In particular, with regard to numerical ranges described in the present specification, arbitrary numerical values and small ranges included in the relevant ranges should be interpreted to be specifically described even where there is no particular description thereof.

REFERENCE SIGNS LIST 1 camera
2 finger
3 first finger guide
4 first transparent plate
5 second finger guide
6 second transparent plate
7 first indicator
8 second indicator
9 first touch sensor
10 second touch sensor
11 hand palm
12 finger base guide
13 wrist guide
14 biometric imaging device
15 placement unit
16 imaging unit
17 determining unit
18 authentication unit
19 transparent plate
20 touch sensor
21 display unit
22 light source

What is claimed is:

1. A biometric imaging device comprising:
a memory storing a program including instructions;
a placement stand including a transparent plate onto which a biological object is placed;
a camera being positioned to take images of said biological object; and
a processor configured to execute the program to perform the instructions including;
controlling the camera to take images of said biological object; and
determining whether or not said biological object is placed on said placement stand based on a feature of said biological object at a place where said placement stand and said biological object are in contact and a feature of said biological object at a place where said placement stand and said biological object are not in contact, in said images;
wherein the transparent plate is configured to support at least a part of the biological object so that said camera takes the images including a part of said biological object that is in contact to the transparent plate and a part which is consecutive to the part of said biological object that is not in contact to the transparent plate.

2. The biometric imaging device according to claim 1, wherein said determining comprises determining whether or not said biological object is placed on said placement stand, based on time variation of a feature of said biological object at a place where said placement stand and said biological object are in contact, in said images.

3. The biometric imaging device according to claim 1, wherein said determining comprises determining whether or not said biological object is placed on said placement stand, based on a comparison of a feature of said biological object at a place where said placement stand and said biological object are in contact, and a feature of said biological object at a place where said placement stand and said biological object are not in contact, in said images.

4. The biometric imaging device according to claim 1, wherein
said feature of said biological object is a profile of said biological object or veins of said biological object; and
said determining comprises determining that said biological object is placed on said placement stand, in a case where the width of the profile of said biological object has become large, or a case where all or part of the veins in said biological object has disappeared, in said images.

5. The biometric imaging device according to claim 1, wherein
said feature of said biological object is veins of said biological object; and
said determining comprises determining that said biological object is placed on said placement stand, in a case where all or part of said veins of said biological object has disappeared at a place where said placement stand and said biological object are in contact, in said images.

6. The biometric imaging device according to claim 1, wherein
said feature of said biological object is a profile of said biological object; and
said determining comprises determining that said biological object is placed on said placement stand, in a case where the width of the profile of said biological object has become large at a place where said placement stand and said biological object are in contact, in said images.

7. The biometric imaging device according to claim 1, wherein
said placement stand has a touch sensor that detects contact by said biological object; and
said determining comprises determining whether or not said biological object is a fake biological object, based on an image of said biological object and a result of the detection by said touch sensor.

8. The biometric imaging device according to claim 1, comprising making a display to prompt that said biological object be placed on said placement stand, in a case where said biological object is not placed on said placement stand.

9. A biometric imaging method, comprising:
taking images of a biological object, by a biometric imaging device; and
determining whether or not said biological object is placed on a placement stand including a transparent plate based on a feature of said biological object at a place where said placement stand and said biological object are in contact and a feature of said biological object at a place where said placement stand and said biological object are not in contact, in said images,
wherein the transparent plate is configured to support at least a part of the biological object so that a camera of the biometric imaging device takes the images including a part of said biological object that is in contact to the transparent plate and a part which is consecutive to the part of said biological object that is not in contact to the transparent plate.

10. A program recorded on a computer-readable non-transient storage medium, wherein the program is configured to execute on a computer:
a process of taking images of a biological object; and
determining whether or not said biological object is placed on a placement stand including a transparent plate based on a feature of said biological object at a place where said placement stand and said biological object are in contact and a feature of said biological object at a place where said placement stand and said biological object are not in contact, in said images, wherein the transparent plate is configured to support at least a part of the biological object so that said camera takes the images including a part of said biological object that is in contact to the transparent plate and a part which is consecutive to the part of said biological object that is not in contact to the transparent plate.

11. The biometric imaging method according to claim 9, wherein a determination is made as to whether or not said biological object is placed on said placement stand, based on time variation of the feature of said biological object at a place where said placement stand and said biological object are in contact, in the images.

12. The biometric imaging method according to claim 9, wherein a determination is made as to whether or not said biological object is placed on said placement stand, based on a comparison of a feature of said biological object at a place where said placement stand and said biological object are in contact, and a feature of said biological object at a place where said placement stand and said biological object are not in contact, in the images.

13. The biometric imaging method according to claim 9, wherein the feature of said biological object is a profile of said biological object or veins of said biological object, and a determination is made as to whether or not said biological object is placed on said placement stand, in a case where the width of the profile of said biological object has become large, or a case where all or part of the veins in said biological object has disappeared, in the images.

14. The biometric imaging method according to claim 9, wherein the feature of said biological object comprises veins of said biological object, and a determination is made that said biological object is placed on said placement stand, in a case where all or part of the veins of said biological object has disappeared at a place where said placement stand and said biological object are in contact, in the images.

15. The biometric imaging method according to claim 9, wherein the feature of said biological object comprises a profile of said biological object, and a determination is made that said biological object is placed on said placement stand, in a case where the width of the profile of said biological object has become large at a place where said placement stand and said biological object are in contact, in the images.

16. The biometric imaging method according to claim 9, wherein the method further comprises: detecting, by a touch sensor, contact by said biological object, and determining whether or not said biological object is a fake biological object based on an image of said biological object and an output result of the touch sensor.

17. The biometric imaging method according to claim 9, further comprising, making a display to prompt that said biological object be placed on said placement stand, in a case where said biological object is not placed on said placement stand.

* * * * *